United States Patent [19]

Burdea et al.

[11] Patent Number: 5,143,505
[45] Date of Patent: Sep. 1, 1992

[54] ACTUATOR SYSTEM FOR PROVIDING FORCE FEEDBACK TO A DEXTROUS MASTER GLOVE

[75] Inventors: Grigore C. Burdea, New York, N.Y.; Jiachen Zhuang, Piscataway, N.J.

[73] Assignee: Rutgers University, New Brunswick, N.J.

[21] Appl. No.: 661,515

[22] Filed: Feb. 26, 1991

[51] Int. Cl.⁵ ............................................. B25J 13/02
[52] U.S. Cl. ........................................ 414/5; 244/234
[58] Field of Search .................. 414/5, 4; 623/63, 64; 244/234

[56] References Cited

U.S. PATENT DOCUMENTS

| | | |
|---|---|---|
| 3,171,549 | 3/1965 | Orloff . |
| 3,263,824 | 8/1966 | Jones et al. . |
| 3,414,137 | 12/1968 | Fortin . |
| 3,449,008 | 6/1969 | Colechia . |
| 3,618,786 | 11/1971 | Fick . |
| 3,637,092 | 1/1972 | George et al. . |
| 3,771,037 | 11/1973 | Bailey, Jr. . |
| 3,995,831 | 12/1976 | Spanski et al. . |
| 4,302,138 | 11/1981 | Zarudiansky . |
| 4,604,016 | 8/1986 | Joyce . |
| 4,795,296 | 1/1989 | Jau . |
| 4,938,487 | 7/1990 | Ponsart ........................... 623/64 X |

OTHER PUBLICATIONS

Paper presented at the "Symposium on Dynamics and Control of Biomechanical Systems":, Dec. 1989 at the ASME winter annual meeting by the inventor.
Information on DATAGLOVE TM Model 2 System from VPL Research, Inc., 656 Bair Island Road, Suite 304, Redwood City, CA 94063.

Primary Examiner—Michael S. Huppert
Assistant Examiner—Donald W. Underwood
Attorney, Agent, or Firm—Mathews, Woodbridge & Collins

[57] ABSTRACT

An actuator system provides force feedback to a dextrous master glove. A first, second and third digit support are connectable by hook and loop fasteners to the thumb, index and middle digits of the glove, respectively. First, second and third actuators comprising pneumatic cylinders extend between the first, second and third digit supports and an "L" shaped palm support mountable on the palm of the glove. Sensors mounted on the back of the glove provide electrical signals that are interpreted by a glove interface and forwarded to a host computer. The host computer computes the movement of the glove and provides feedback through a digital-to-analog circuit, and an actuator interface to the first, second and third actuators. Sphere joints connect the first, second and third actuators to the palm support. Each sphere joint includes an air passageway that communicates with the pneumatic force feedback cylinders in the actuators. Cylindrical joints connect the first, second and third digit supports to the first, second and third actuators. The spherical joints permit rotation in a cone of about 60° and provide for realistic three-dimensional manipulation in a compact environment.

13 Claims, 7 Drawing Sheets

ACTUATOR SYSTEM FOR PROVIDING FORCE FEEDBACK TO A DEXTROUS MASTER GLOVE

CROSS-REFERENCE TO RELATED INVENTIONS

This application is related to copending U.S. patent application Ser. No. 07/396,476 filed Aug. 21, 1989 by Grigore C. Burdea and entitled PORTABLE DEXTROUS FORCE FEEDBACK MASTER FOR ROBOT TELEMANIPULATION, now U.S. Pat. No. 5,004,391 issued on Apr. 2, 1991, the entire text and contents of which are hereby incorporated by reference into this application.

BACKGROUND OF THE INVENTION

1. Field of the Invention

This invention relates to an actuator system for use with a dextrous master glove for providing force feedback to the glove as a function of glove manipulation.

2. Description of Related Art

Present telemanipulation techniques include the use of mechanical masters, open-loop servomasters, and to a lesser extent, closed-loop servomasters. Direct mechanical telemanipulation is often the simplest method, but cannot be used in applications where the slave is not in the immediate vicinity of the master. Closed-loop telemanipulation eliminates the proximity requirement but may necessitate the need to have two nearly identical devices to act as master and slave. This duplication of resources is often prohibitive in terms of cost and payload weight.

Efforts have been made to eliminate the duplicate master by replacing it with force feedback joysticks, sensorized spheres, pistol grips and the like. Although such devices have served their purposes, they have not proved entirely satisfactory under all conditions of service because these devices are less "natural" to an operator since direct similitude does not exist between human hand and robot finger motions. Examples of manual controllers using levers, grippers, handles and the like, with some having force, feedback, may be found in the following U.S. Pat. Nos.: 4,795296; 3,995,831; 4,604,016; 3,618,786; 3,637,092 and 3,771,037.

Those concerned with the development of telemanipulation devices have recognized the disadvantages of such prior art controllers and the need for a dextrous master controller that uses an operator's hand to replace the classical manipulation arm, the conventional keypad contact, the joystick or handle, or other similar structure. Use of the human hand is a natural form of control and is applicable for use with both non-dextrous and dextrous slave devices. Further, because the human hand is used as master, duplication of most hardware is not required and weight, inertia and friction can be reduced. Under most conditions, significant improvements in the time necessary to complete a task can be realized when using the human hand as the master. For example, it has been estimated that an improvement on the order of 10 can be expected on time efficiency when a dextrous master is used in place of a conventional keypad control.

While open-loop dextrous masters create more natural control environments, they lack the ability to bring force feedback to the operator's hand, which in turn limits the utility of the slave device. However, a dextrous master with force feedpack, using much of the human hand as master in a closed-loop teleoperations environment, will allow the efficient execution of complex tasks such as assembly and repair involving the telemanipulation of small, intricately-shaped parts. Examples of robotic masters with force feedback and wherein much of the human hand is used as the master may be found in the following U.S. Pat. Nos.: 3,449,008; 3,171,549 and 4,302,138.

U.S. Pat. No. 3,414,137 entitled REMOTE HANDLING DEVICE issued Dec. 3, 1968 to Marcel Fortin is typical of telemanipulation devices that employ a squeezable, manipulatable device for remote control. A hand grabbable grip is squeezed causing the remote flexing of a pair of robotic fingers around an object. This device is especially adapted for use in nuclear reactors or dangerous environments.

U.S. Pat. No. 4,302,138 entitled REMOTE HANDLING OF DEVICES issued on Nov. 24, 1981 to Alain Zarudiansky, describes a device for improving the grip and remote handling of an object. An artificial hand, or slave hand, is remotely controlled by the hand of an operator. Sensors on the artificial hand provide for the sensing of tactile parameters. The signals produced by the sensors are applied to actuators located on the backside of the master hand. The master hand may be in the form of a modified glove in which the hand of the operator is inserted. The actuators mounted on the backside glove supply tactile sensations to the hand of the operator. Thus the operator apparently "feels" the object as if the object were being handled directly by the operator. This particular device is especially useful for the handling of objects in dangerous environments, such as in the nuclear or chemical industries, or possibly may be used by an operator in outer space or underwater. The major drawback of such a device is that it is fairly bulky because it requires the sensing and manipulation of the hand from the backside. The hand thus loses a lot of its "feel" because the "feel" of a hand is from the palm not the outside. Thus, the device such as set forth in U.S. Pat. No. 4,302,138 is significantly larger and less effective than the device set forth in the present disclosure.

The foregoing examples demonstrate various prior art attempts to obtain a controller that is more "natural" to the operator. There has been long recognized a need for "natural" dextrous masters that more closely simulate the motions of the finger of a dextrous slave. Unfortunately, no practical system has yet been devised for doing so. Ideally, such a system would have the capability of being hand-holdable in an actual position in the operator's hand. It would also be operable by the operator using natural motions and would be relatively lightweight. A force feedback mechanism would be provided back to the operator's hand in a manner that corresponds directly to the forces generated on the slave. Moreover, the device should be compact, portable, simple in construction and dependable in operation.

In an attempt to solve the foregoing challenge, the inventor discovered a technique and mechanism set forth in U.S. application Ser. No. 07/396,476 and entitled PORTABLE DEXTROUS FORCE FEEDBACK MASTER FOR ROBOT TELEMANIPULATIONS, now U.S. Pat. No. 5,004,391. The entire contents of which is incorporated by reference into this disclosure. The actuator device described therein includes a compact, hand-held unit that fits within the space defined by the user's palm and fingers and functions as a position controller for a robot having a slave hand. A finger position sensor including a linear, variable differential transformer provides an output signal that is proportional to the distance between the user's fingers. A force feedback system, including a pneumatic microactuator, senses the forces exerted by the end effectors of the robot hand and causes a corresponding force to be exerted on the fingers of the user. The foregoing invention was intended primarily for use between the thumb and middle finger of the operator's hand. As such, it limited the ability to provide force feedback between any other fingers of the hand and also required the usage of a special sensor system using a linear differential transformer between the two manipulating digits. However, there now exists on the market sensor-type gloves such as the DataGlove ™ Model 2 available from VPL Research, Inc., 656 Bair Island Road, Suite 304, Redwood City, Calif. 94063 which senses the position of the fingers and provides information with regard to position and orientation to a host computer for a variety of different purposes. A Polhemus-type sensor mounted on the backside of the glove, provides information with regard to the motion of the wrist in space. Sensor gloves such as the DataGlove ™ typically include fiber optic sensors that are located on the back, i.e. topside, of the glove such that the movement of the fingers is sensed by the fiber optic sensors and transmitted through a fiber optic umbilical bundle back to a glove interface. The glove interface suitable for use with a standard host computer is also available from VPL Research, Inc.

The concept of employing a sensor-type glove in the context of a force feedback system was described in a paper presented at the "Symposium on Dynamics and Control of Biomechanical Systems" Dec. 1989 at the ASME winter annual meeting by the inventor. The present invention is an improvement over the device described in that paper and in the invention set forth in applicant's co-pending application.

SUMMARY OF THE INVENTION

Briefly described, the invention comprises an actuator system for providing force feedback to a dextrous master glove. The dextrous master glove, such as the DataGlove ™, typically includes a plurality of fiber optic sensors located on the backside of the glove for detecting movement of the digits. A hand is considered to have five digits, namely four fingers (index, middle, ring and small fingers) and an opposed thumb. A linkage or a Polhemus-type sensor can be mounted on the back of the glove to provide information with regard to the position and orientation of the wrist. While such devices are adequate for the purpose of providing sensory input to computers with regard to the movement of the hand and digits, the use of such devices with force feedback mechanisms that provide a "natural" feel is limited. According to the present invention, a first, second and third digit support are connectable by hook and loop fasteners to the thumb, index and middle digits of the glove, respectively. The hook and loop fasteners are preferably of the well-known Velcro ® variety manufactured by Velcro USA, Inc., 406 Brown Avenue, Manchester, N.H. 03108. First, second and third actuators comprising pneumatic cylinders extend between the first, second and third digit supports and an "L" shaped palm support mountable on the palm of the glove. The "L" shaped palm support has a first leg and a second leg. Sphere-type joints connect the first, second and third actuators to the "L" shaped palm support. The actuator between the thumb and the palm support is connected by its sphere joint to the first leg of the "L" shaped palm support. The other two actuators connected between the index finger and middle finger to the palm support both share the second leg of the "L" shaped palm support in common. Each sphere joint includes an air passageway that communicates with the pneumatic force feedback cylinder in the actuators. Pin type cylindrical joints connect the first, second and third digit supports to the first, second and third actuators. The sensors mounted on the back of the master glove provide electrical signals that are interpreted by a conventional glove interface, available commercially, and forwarded to a commercially available UNIX based host computer. The host computer computes the movement of the glove and provides force feedback instructions through a digital-to-analog circuit and an actuator interface to the first, second and third actuators, respectively.

The spherical joints permit the rotation of the thumb, index and middle fingers in a cone of about 60°. Because all of the actuators are mounted between the digits and the palm, it provides for a realistic, natural feeling response as a result of the remote manipulation of an object by a robot slave hand. The device is also more realistic in that it is compact and easy to use.

The foregoing features will be better understood by reference to the following drawings.

DETAILED DESCRIPTION OF THE INVENTION

During the course of this description, like numbers will be used to identify like elements according to the different views that illustrate the invention.

Figure 1:
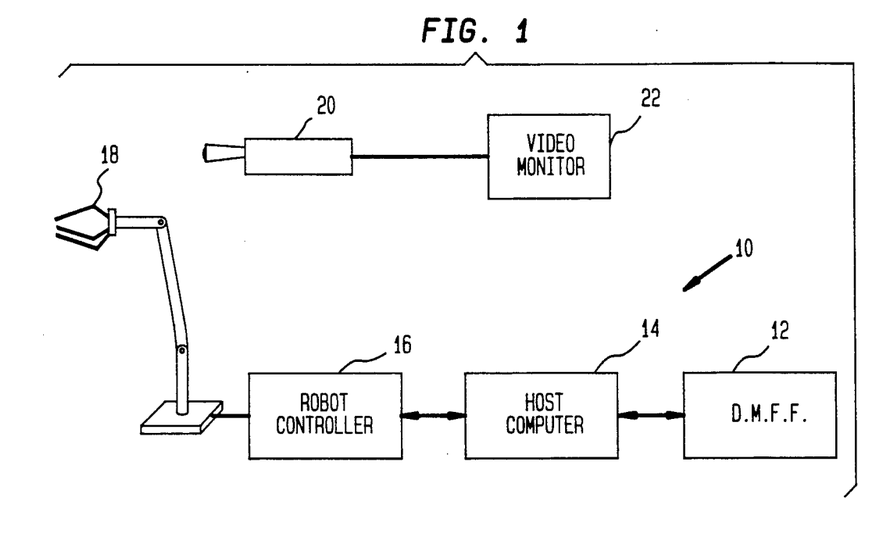
FIG. 1 is a schematic block diagram of the preferred environment of the invention showing the dextrous master with force feedback (D.M.F.F.) manipulating a remote slave hand and providing visual feedback to the operator through a video monitor system.

FIG. 1 illustrates the preferred environment 10 of the invention 12. A dextrous master glove having force feedback ("D.M.F.F.") 12 provides input to a conventional host computer 14. The host computer 14 can be almost any commercially available UNIX based system. In the preferred environment 10, a Model SUN 4-260 SPARC TM station from Sun Microsystems, 2550 Farcia Avenue, Mountain View, Calif. 94043 was employed. The preferred embodiment of the D.M.F.F. 12 is illustrated in further detail in FIGS. 4–5E. Host computer 14 receives signals from the sensors on the D.M.F.F. 12 and converts them into control signals for robot controller 16. A slave hand 18 responds to the instructions from the robot controller 16 to duplicate the motions of the D.M.F.F. 12. Conventional sensors, not shown but known to those of ordinary skill in the art, respond to reaction pressures exerted on the slave hand 8 by objects to be grasped. The reaction signals are transmitted back through robot controller 16 and host computer 14 as force feedback instructions to the D.M.F.F. 12. The preferred embodiment of the environment 10 may also include a video camera 20 and a video monitor 22 to provide visual feedback to the operator 34 as illustrated in FIG. 2B.

Figure 2A:
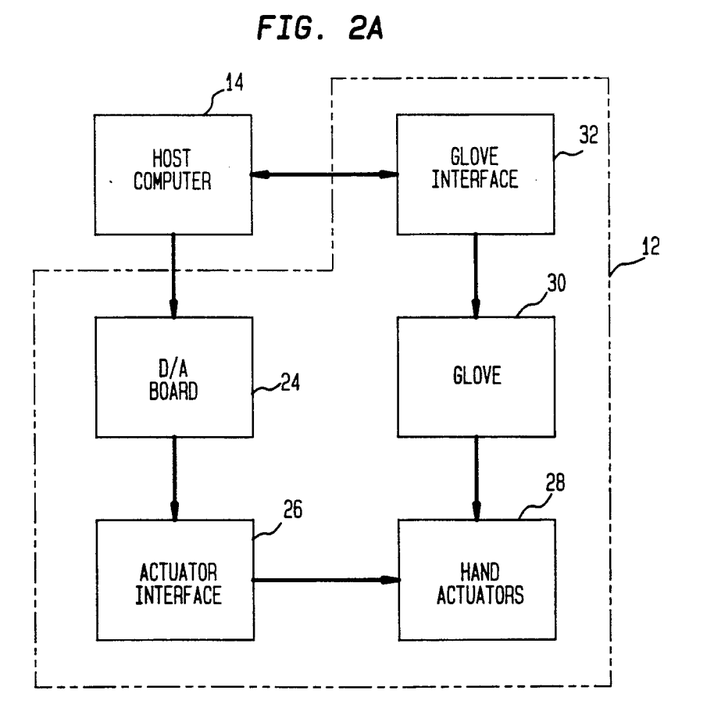
FIG. 2A is a block diagram illustrating the overall system of the present invention.

FIG. 2A is a block diagram which illustrates the details of the D.M.F.F. system 12 as it interacts with host computer 14. The operator 34 begins by placing his or her hand in a glove 30 having sensors mounted on the back. A glove 30 acceptable for the purpose is the Data-Glove TM Model 2, previously disclosed. Fiber optic sensors 72 mounted on the back of the glove 30 create signals which pass through an umbilical cord 74 to a glove interface 32. The sensors 72 measure the movement and position of each of the five digits. A Polhemus-type sensor 76 mounted on the back 60 of the glove 30 provides information with respect to the orientation and position of the wrist. According to the preferred environment 10, a Model "3 space Isotrack" sensor made by Polhemus Navigation Sciences, Colchester, Vt. was employed An acceptable glove interface 32 is also manufactured by VPL Research, Inc. Digit position and hand orientation are relayed through glove interface 32 to the host computer 14. Host computer 14 acts as a gateway to transmit instructions to a robot hand 18 in an environment such as set forth in FIGS. 1, 6 or 7. Feedback forces responding to the pressure exerted by the slave hand 18 are transmitted back through the host computer 14 to a conventional digital-to-analog circuit board 24. The analog signals from D/A board 24 direct the actuator interface 26 to supply pneumatic pressure to the hand actuator system 28 located in the palm 58 of the sensor glove 30. Details of the actuator interface 26 are described in FIG. 3. The actuators 78a, 78b and 78c that comprise the actuator system 28 provide force feedback to the thumb 62, index 64 and middle 66 fingers of the sensor glove 30. The force feedback is very natural and simulative of the real experience an operator 34 would have if he or she directly manipulated the remote object handled by the robot slave hand 18.

Figure 2B:
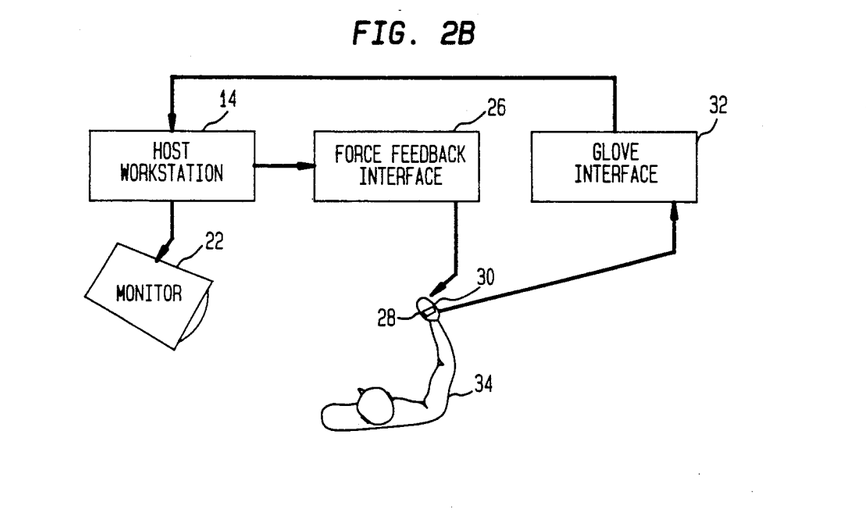
FIG. 2B is another block diagram illustrating the overall system of FIG. 2A under the control of a human operator.

FIG. 2B illustrates the preferred environment 10 of the invention shown in FIG. 1 with an operator 34 in position in front of monitor 22.

Figure 2C:
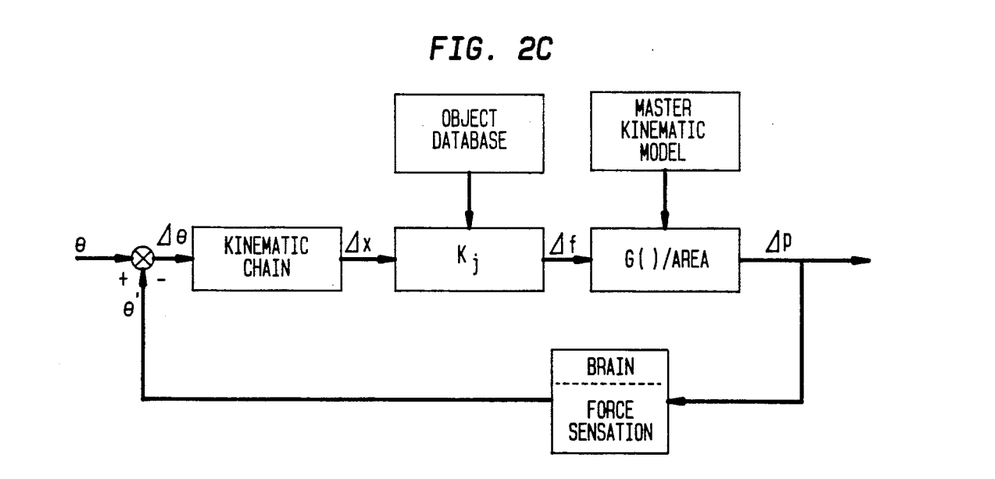
FIG. 2C is a closed control loop block diagram of the system illustrated in FIGS. 2A and 2B.

FIG. 2C is a simplified schematic representation of the closed control loop of the force feedback system. Data $\Delta \Theta$ from the sensors 72 and 74 mounted on the back or topside 60 of glove 30 provide input to a feedback point. That data $\Delta \Theta$ is transformed $\Delta$ x into linear information and compared against an object data base to produce a desired force $\Delta$ f. That information is then compared against a master kinematic model to produce the appropriate change in pressure $\Delta$ P in the actuator structure 28. force sensation to the feedback point contributes to the operator's decision making, determining a new angle $\Theta'$. There may also be visual feedback to the operator's brain by means of a video camera 20 and a video monitor 22 such as illustrated in FIGS. 1 and 2B.

Figure 3:
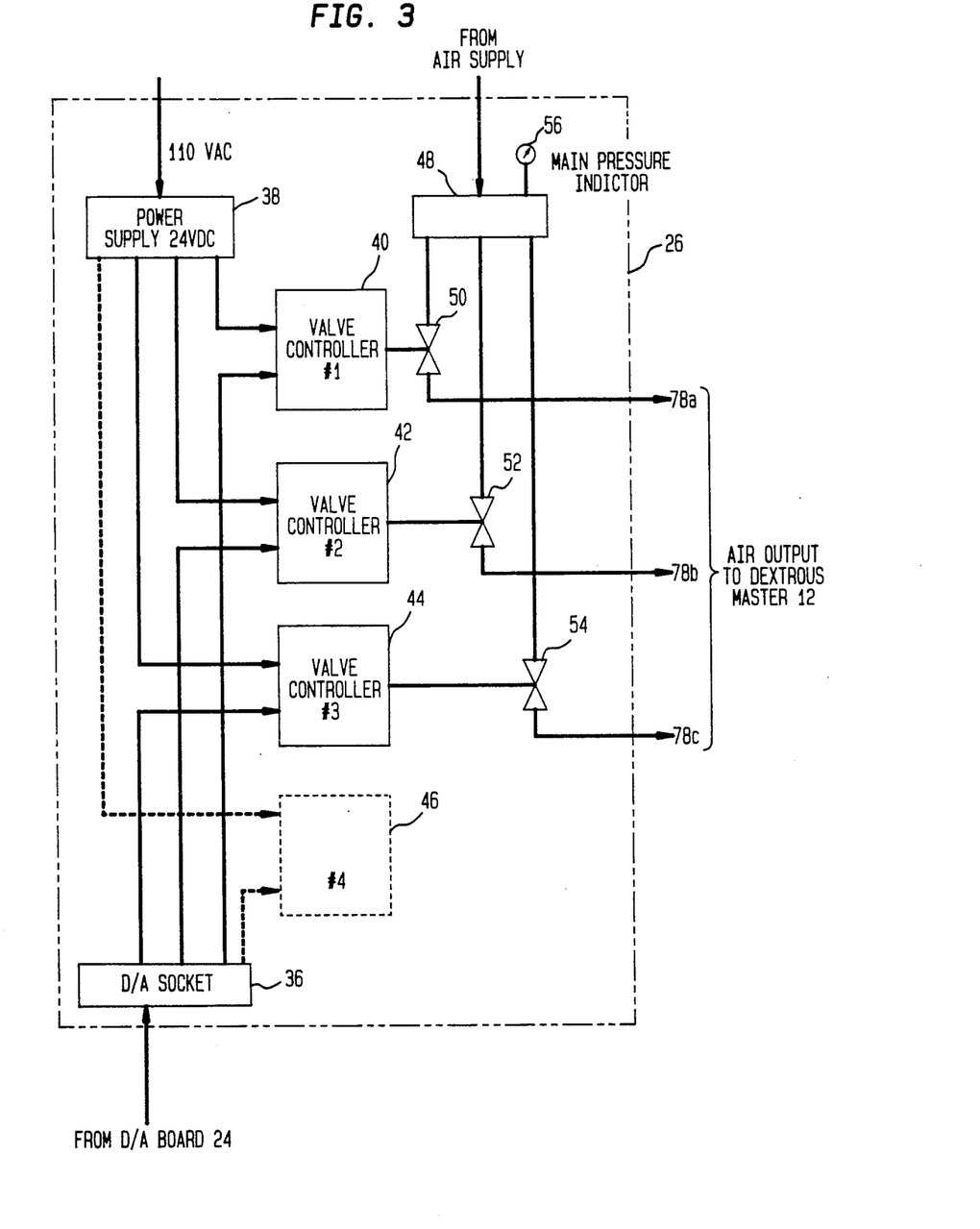
FIG. 3 is a block diagram illustrating the component of the actuator interface.

Details of the actuator interface 26 are shown in the block diagram of FIG. 3. Analog signals from the digital-to-analog board 24 are received by D/A socket 36 and are passed as control signals to valve controller #1 (40), valve controller #2 (42), valve controller #3 (44) and, if desired, a valve controller #4 (46). Valve controller 46 is used when four digits are provided with force feedback (i.e. when a structure with four actuators is used). 110V AC power is stepped down by power supply 38 to 24V DC and provides the other input to valve controllers 40, 42, 44 and 46. Air pressure is provided through manifold 48 to pneumatic valves 50, 52 and 54 which are controlled, respectively, by valve controllers 40, 42 and 44. Analog signals from the digital-to-analog board 24 pass through the D/A socket 36 to control valve controllers 40, 42 and 44 which in turn direct valves 50, 52 and 54, respectively, to pass pressurized air to actuators 78a, 78b and 78c. Main pressure indicator gauge 56 measures the pressure in the manifold 48 in order to insure that it is sufficiently high to drive the hand actuator system 28.

Figure 4:
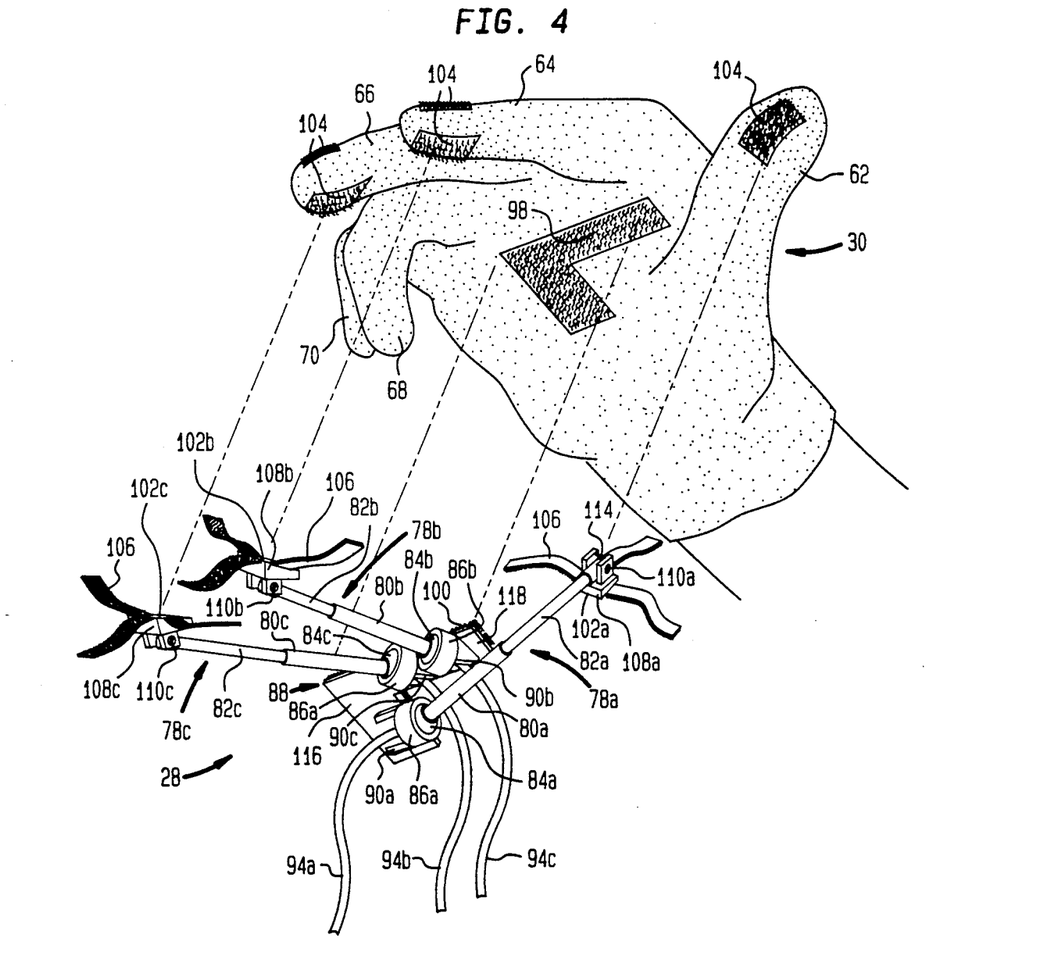
FIG. 4 is an exploded view of the preferred embodiment of the actuator system in the context of a dextrous master glove having sensors mounted on the back thereof.
Figure 5A:
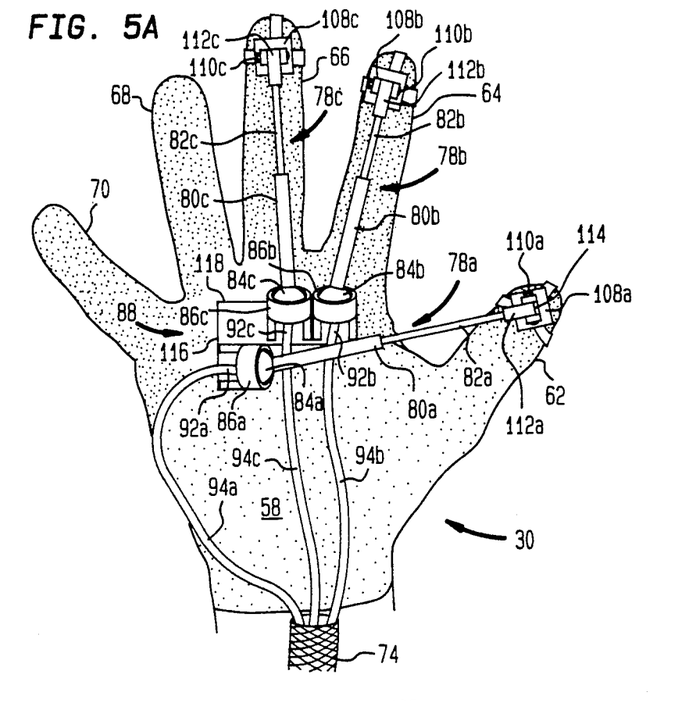
FIG. 5A is a front elevational view of the actuator system in the palm of the dextrous master glove.
Figure 5B:
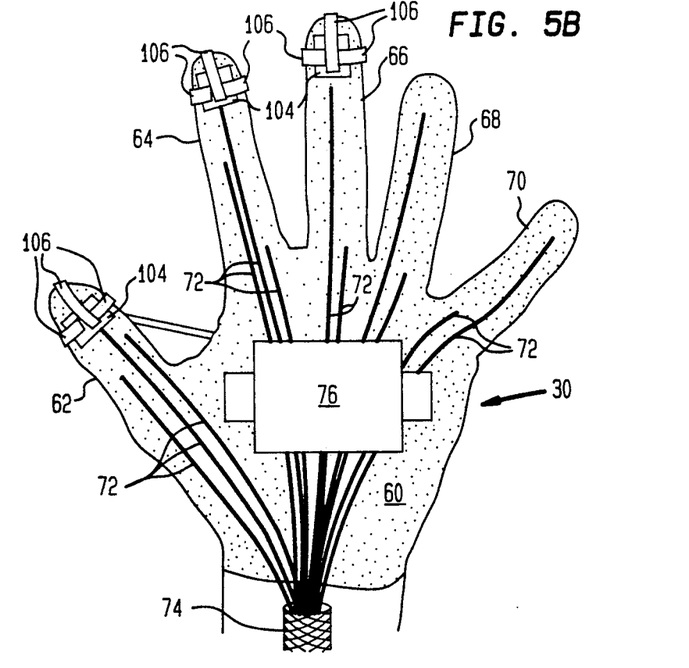
FIG. 5B is a rear elevational view of the actuator system and glove illustrated in FIG. 5A.

FIG. 4 is an exploded view of the hand actuator system 28 and glove 30 as seen from below the palm 58 of the glove 30. The glove 30, preferably like the Data-Glove TM, previously described, includes a thumb digit 62, an index finger digit 64, a middle finger digit 66, a fourth or ring finger digit 68 and a little finger digit 70. Conventional fiber optic sensors 72 are mounted on the backside of the digits 62–70 as shown in FIG. 5B. The output from the optical sensors 72 passes through an umbilical cord 74 to the glove interface 32. A Polhemus sensor 76 may be mounted on the back 60 of the glove 30. Polhemus sensor 76 works in conjunction with an externally generated electromagnetic field to provide input relative to the position and orientation of the wrist of the operator 34. Leads from the fiber optic sensors 72 and the Polhemus sensor 76 as well as the pneumatic hoses 94a, 94b and 94c all pass through the same umbilical cord 74 for convenience.

The hand actuator system 28 is located in the palm 58 of the glove 30 and comprises three actuators 78a, 78b and 78c which can apply pressure from the palm 58 against the thumb digit 62, index finger digit 64 and the middle finger digit 66, respectively.

The hand actuator system 28 is mounted on an "L" shaped base 88 having two legs 116 and 118. The first leg 116 is shorter than the second leg 118 and at right angles thereto. A sphere joint mounting block 90a supports a sphere joint housing 86a which, in turn, surrounds a sphere joint 84a. As shown in FIG. 5E, a pass through pneumatic fitting 92a accommodates pneumatic hose 94a which passes through sphere joint 84a to cylindrical body 80a of actuator 78a. A movable piston rod 82a sits within cylindrical body 80a. A pin engaging head 112a sits on top of piston rod 82a and engages a cylindrical pin 110a mounted on wedge-shaped mounting section 108a as can be seen in FIGS. 4 and 5A. Wedge-shaped mounting In a similar fashion, the other two sphere mounting blocks 90b and 90c are mounted in parallel on the long second leg 118 of the "L" shaped base 88. Sphere joint housings 86b and 86c are supported by the sphere joint mounting blocks 90b and 90c and enclose sphere joints 84b and 84c. Each of the sphere joints 84b and 84c includes a pass through pneumatic fitting 92b and 92c for pneumatic hoses 94b and 94c, respectively, from the actuator interface 26 as illustrated in FIGS. 2A and 3. The air supplied by interface 26 passes through the sphere joints 84b and 84c into the cylindrical bodies 80b and 80c of actuators 78b and 78c. Piston rods 82b and 82c fit within cylindrical bodies 80b and 80c and are adapted to move in and out in response to the air pressure from the actuator interface 26. Piston rods 82b and 82c are equipped with pin engaging heads 112b and 112c which attached to cylindrical pins 110b and 110c for movement in a two-dimensional plane with respect to each digit to which it is attached. Cylindrical pins 110b and 110c are mounted on wedges 108b and 108c which, in turn, are attached to the index and middle bases 102b and 102c, respectively. Wedge or prism-shaped elements 108a, 108b and 102c ensure that the feedback pressure supplied to the digits 62, 64 and 66 is relatively perpendicular to the tips of those digits where a grasping motion is executed. The cylindrical bearing pins 110a, 110b and 110c in combination with the pin engaging heads 112a, 112b and 112c are essentially identical except that the thumb wedge 108a includes a stop bar element 114 to prevent the thumb digit 62 from bending too far with respect to the thumb actuator 78a.

The actuator system 28 is preferably separable from the sensor glove 30. According to the preferred embodiment, hook-type material 100 is attached to the bottom of the "L" shaped base 88 and is adapted to selectively mate with hook-type material 98 located in the palm 58 of glove 30. Similarly, loop-type material 104 on the palm side upper surface of thumb digit 62, index finger digit 64 and middle finger digit 66 are adapted to mate with a hook-type material 106 on the bottom of bases 102a, 102b and 102c. The hook-type material 106 may also pass around to the top or backside of the upper digits 62, 64 and 66 so that a "T" shaped piece of hook material 106 can wrap around to the backside of the digits for better engagement with another piece of loop material 104.

Details of the hand actuator system 28 in the context of a sensor glove 30 are shown in FIGS. 5A and 5B, respectively. FIG. 5A is a front view of the hand actuator system 28 shown mounted on the palm 58 of glove 30. Conversely, FIG. 5B is a rear view of the same glove 30 with the actuator system mounted on the back 60.

Figure 5C:
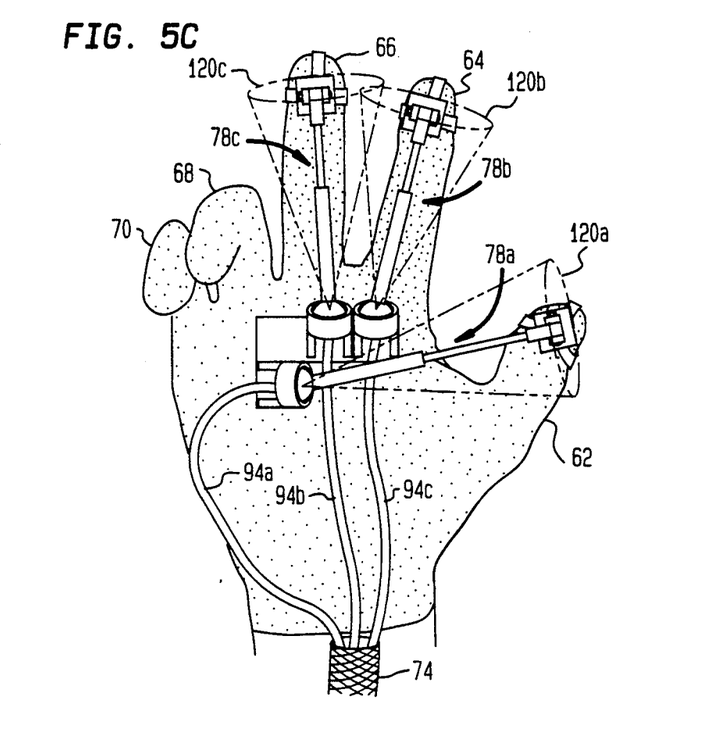
FIG. 5C is a frontal view illustrating the cones of rotation available to the thumb, index and middle fingers using the actuator system according to the present invention.
Figure 5D:
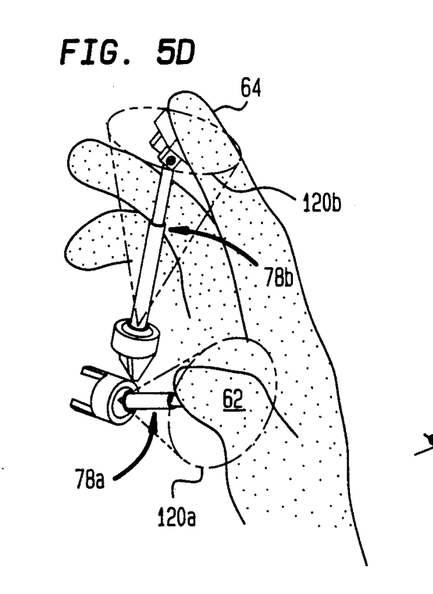
FIG. 5D is a lateral view of the cones of rotation illustrated in FIG. 5C.
Figure 5E:
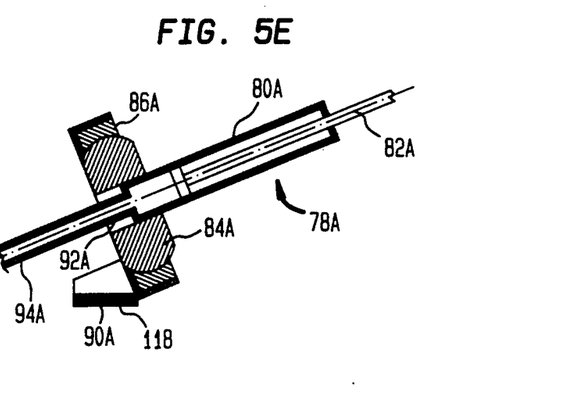
FIG. 5E is a detail cross-sectional view of a single sphere joint showing the air passageway therethrough.

FIGS. 5C and 5D, respectively, illustrate how the present invention 12 provides maximum independent movement for maximum effective control. Each sphere joint 84a, 84b and 84c defines a cone 120a, 120b and 120c, respectively, of about 60° with the upper limit given by the stroke of the piston rods 82a, 82b and 82c. The cylinders 80a, 80b and 80c are mounted coaxially with the sphere joints 84a, 84b and 84c, thus allowing for direct connection to the three small air tubes or hoses 94a, 94b and 94c that pass through the sphere joints 84a, 84b and 84c, respectively. These details may be further appreciated by referring to FIG. 5E. Each cylindrical piston rod 82a, 82b and 82c is attached to the fingertips of the finger digits 62, 64 and 66 through the cylindrical joints that comprise the pins 110a, 110b and 110c that allow the maximum movement in the axial (i.e. two-dimensional) plane of the fingers 62, 64 and 66. The foregoing maximum movement is achievable by making the finger actuators 78a, 78b and 78c oppose the palm 58 from the other digits 62, 64 and 66. The freedom of movement is further enhanced by separating the sphere mounting blocks 90a, 90b and 90c with their housings 86a, 86b and 86c from each other as far as possible and by mounting the thumb digit actuator 78a on the short leg 116 of "L" shaped base 88, thereby putting it in a different plane with the other two actuators 78b and 78c, which are mounted on the long leg 118 of the "L" shaped base 88. The foregoing provides for maximum simulation of real feedback in a lifelike setting. For example, if the operator 34 were to direct the robot slave hand 18 to pick up an orange, the force feedback to the sensor glove 30 provided by the actuator system 28 would provide individual realistic feedback to each of the digits 62, 64 and 66. It will be appreciated from FIGS. 5C and 5D that each conic envelope 120a, 120b and 120c does not interfere significantly with the other. The sphere joints 84a, 84b and 84c provide for three degrees of freedom while the cylindrical pin bearings 110a, 110b and 110c provide for two degrees of freedom. It has been found that three feedback actuators 78a, 78b and 78c are sufficient to provide realistic response in view of the fact that the thumb, index and middle digits 62, 64 and 66, respectively, provide most of the manipulation of a hand. However, it would be possible to expand the system to provide feedback actuators 78 to the fourth or ring finger 68 and/or the little finger 70. Nevertheless, three to four actuators 78 are sufficient for most purposes because five fingers may provide too much redundancy.

The use of hook and loop material 98, 100, 104 and 106 such as the well known Velcro ® has two advantages. First, it allows the actuator system 28 to be removed completely from the sensor glove 30 so that the glove 30 can be used without the actuators 28. Second, and perhaps more importantly, it allows the actuator system 28 to be calibrated against each person's hand. In this manner, the attachment 28 to the glove 30 can be customized so that the fit is proper from operator to operator.

The prism-shaped wedge mounting sections 108a–c are important because they allow motion to the fingertips 62, 64 and 66 which is relatively normal to the fingertips. This is a more natural feeling since reaction forces on the human hand are more likely to be normal to the surface of the skin rather than parallel with respect thereto.

Prior art feedback actuators typically provided one degree of freedom. The present invention is much more flexible and provides both in and out manipulation as well as full lateral manipulation in the context of at least three to five independently operable actuators 78. The foregoing, since it fits within the palm of the glove 30, is relatively small and compact compared to prior art devices.

The Polhemus sensor 76 operates at 30 Hz and provides real time measurements of the position and orientation of the wrist of the glove 30.

Pressurized air with a pressure of up to 110 psi is applied through the manifold 48 and through valves 50, 52 and 54 to actuators 78a, 78b and 78c. It is possible that hydraulic pressure could also be used but it is not as convenient in the context since relatively low feedback forces are required. For applications of very high feedback forces, perhaps hydraulic fluids might be a possibility.

The use of a sphere joint 84a–c having a pneumatic fitting 92a–c that passes through the joint is very useful in the context of the present invention because it avoids any fixed resistance that could be due to lateral motion if the pneumatic hoses 94a, 94b and 94c were connected directly to the cylinders 80a, 80b and 80c. This further dramatically enhances the realistic independent "feel" of the actuator system 28.

In summary, the actuator system 28 provides real pressure feedback to a sensor glove 30. Also important is the fact that the actuator system 28 is very lightweight and in its entirety weighs about 45-50 grams (i.e. approximately 0.1 pounds). The use of plastic and other lightweight materials can further reduce the weight of the actuator system 28 to the point where the operator 34 bearly notices its presence.

Figure 6:
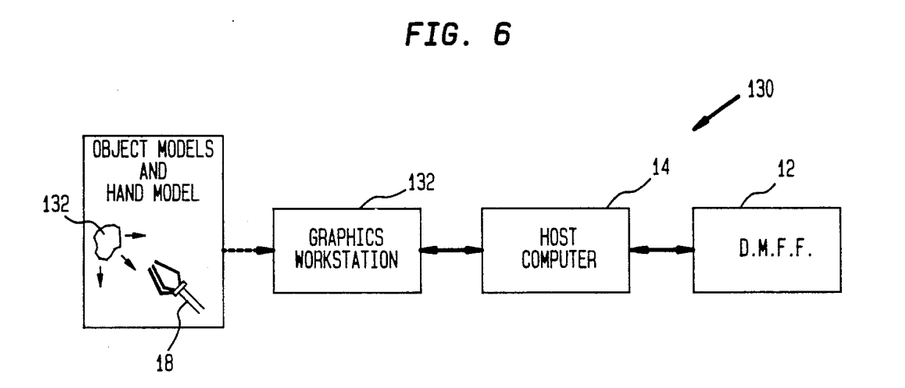
FIG. 6 illustrates an alternative embodiment of the actuator system in the context of an artificial reality environment.

The actuator system 28 in conjunction with the D.M.F.F. 12 can be used in environments other than that described in FIG. 1. For example, the system can be used as part of an artificial reality environment 130 as illustrated in FIG. 6. In the artificial reality environment 130, the D.M.F.F. 12 interacts with a host computer 14 as previously described. The output thereof provides an input to a graphics workstation 132 which, with the appropriate instructions, controls a pseudo robot slave hand or model of a human hand 18 and pseudo objects 132. The artificial feedback from the graphics workstation 132 returns to the host computer 14 and is provided to the D.M.F.F. 12 in the form of an artificial force feedback in response to the pseudo environment generated by the graphics workstation 132 and the host computer 14. The response of the D.M.F.F. 12 is, however, the same for the artificial force feedback, as in a real environment.

Figure 7:
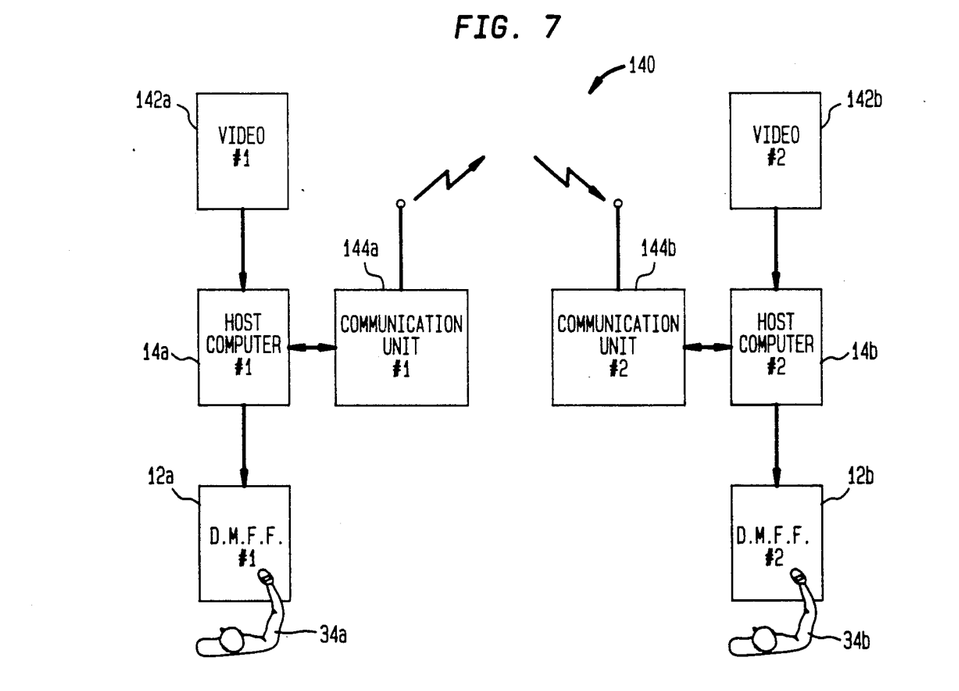
FIG. 7 illustrates another alternative embodiment of the actuator system in the context of a teleconferencing environment.

Another interesting alternative environment for the D.M.F.F. 12 and the actuator system 28 is shown in FIG. 7. A teleconferencing environment 140 is illustrated in which an operator 34a manipulating a first D.M.F.F. 12a can virtually shake hands with another operator 34b using a second D.M.F.F. 12b. The first operator 34a, manipulating the first D.M.F.F. 12a provides input to a first host computer 14a and the output thereof is transmitted by a first communications unit 144a. Signals are received by a second communications unit 144b and are transmitted to a second host computer 14b which in turn supplies signals to a second D.M.F.F. 12b and a second video monitor 142b. The first video monitor 142a, including a camera in both instances, is likewise connected to the first host computer 14a. In operation, the teleconferencing environment 140 might operate as follows. The first operator 34a manipulating the first D.M.F.F. system 12a might reach out to shake hands with the second operator 34b employing the second D.M.F.F. 12b. The first operator 34a can see the second operator 34b on the video camera and monitor system 142a. The reaching out motion is interpreted by the first host computer 14a and transmitted by the first communications unit 144a. The signals are received by the second communications unit 144b and transmitted to the second host computer 14b. A picture of the first operator 34a will appear on the second video monitor 142b. Simultaneously, the second D.M.F.F. 12b will produce a gripping motion similar to that produced by the first operator 34a on the first D.M.F.F. 12a. In response thereto, the second D.M.F.F. operator 34b will feel the simulated motion of the first operator 34a and, will probably reciprocate by returning the hand clasp which will be interpreted by the second host computer 14b and transmitted via the second communications unit 144b to the first communications unit 144a and interpreted by the first host computer 14a as a force feedback to the first operator 34a via the first D.M.F.F. system 12a. In the foregoing fashion, it is possible for the first operator 34a to shake hands with the second operator 34b and the second operator 34b to shake hands with first operator 34a in a manner that simulates the realistic tactile sensations of the actual handshaking experience. Subsequently, both operators, 34a and 34b, may interact with an object, for example, a textile sample to be be sold. They both "feel" it and then negotiate the sale.

While the invention has been described with reference to the preferred embodiment thereof, it will be appreciated by those of ordinary skill in the art that modifications can be made to the structure and functions of the system without departing from the spirit and scope of the invention as a whole.

I claim:

1. An actuator system for use with a glove having a palm surface, a plurality of digits and back surface with a plurality of sensors mounted thereon for generating electrical signals responsive to the movement of said digits, said system comprising:
   a first digit support connectable to a first digit of said glove;
   a palm support spaced from said first digit support and positionable on the palm surface of said glove;
   a first actuator means comprising a pneumatic cylinder, extending between said supports for providing force feedback to said first digit support as a result of electrical signals generated by at least one of said sensors; and,
   a first sphere joint for connecting said first actuator means to said palm support, said first sphere joint including an air passageway for communicating with said first pneumatic cylinder.

2. The system of claim 1 further comprising:
   a second digit support connectable to a second digit of said glove;
   a second actuator means comprising a second pneumatic cylinder extending between said second digit support and said palm support for providing force feedback to said second digit support as a result of electrical signals generated by at least one of said
   wherein one of said digits of said glove is a thumb and one of said actuator means is located between the palm support and said thumb.

3. The system of claim 2 further comprising:
   a second sphere joint for connecting said second actuator means to said palm support, said second sphere joint including an air passageway therein for communicating with said second pneumatic cylinder.

4. The system of claim 3 further comprising:

a third digit support connectable to a third digit of said glove; and, a third actuator means comprising a third pneumatic cylinder extending between said third digit support and said palm support for providing force feedback to said third digit support as a result of electrical signals generated by at least one of said sensors.

5. The system of claim 4 further comprising:

a third sphere joint connected between said third actuator means and said palm support, said third sphere joint including an air passageway therein for communicating with said third pneumatic cylinder.

6. The system of claim 5 further comprising:

first, second and third cylindrical joints located between said first, second and third digit supports and said first, second and third actuator means, respectively.

7. The system of claim 6 further comprising:

attachment means for selectively attaching said first, second and third digit supports and said palm support to said glove.

8. The system of claim 7 wherein said attachment means comprises a first material for selectively mating with a second material, wherein one of said materials comprises a hook-type material and said other type of material comprises a loop-type material for mating with said hook-type material.

9. The system of claim 8 wherein said palm support has a generally "L" like shape having a first and a second leg, wherein one of said sphere joints is mounted on said first leg and the remaining two sphere joints are mounted on said second leg of said palm support.

10. The system of claim 9 further comprising:

first, second and third mounting means located between said first, second and third digit supports and first, second and third actuator means, respectivley, for providing feedback force that is substantially perpendicular to the tip of said first, second and third digits, respectively.

11. The system of claim 10 wherein said first, second and third mounting means, respectively, comprise prism shaped mounting elements.

12. The system of claim 11 further comprising:

stop means mounted on said mounting means connectable to the thumb of said glove for limiting the travel of its respective cylindrical joint.

13. The system of claim 12 wherein said glove comprises a flexible glove for covering the hand of the user on the inside and including said plurality of sensors mounted on the outside thereof.

* * * * *